United States Patent [19]

Higashidate et al.

[11] Patent Number: 5,013,443
[45] Date of Patent: May 7, 1991

[54] EXTRACTION AND SEPARATION METHOD AND APPARATUS USING SUPERCRITICAL FLUID

[75] Inventors: Sakae Higashidate, Hachioji; Yoshio Yamauchi, Hino; Muneo Saito, Hachioji, all of Japan

[73] Assignee: Nihon Bunko Kogyo Kabushiki Kaisha, Tokyo, Japan

[21] Appl. No.: 465,706

[22] Filed: Jan. 16, 1990

[30] Foreign Application Priority Data

Jan. 23, 1989 [JP] Japan .................................. 1-14532

[51] Int. Cl.$^5$ .......................................... B01D 11/04
[52] U.S. Cl. .................................. 210/634; 210/656; 210/198.2; 210/511; 260/412; 260/412.8; 260/428.5
[58] Field of Search ............... 210/634, 639, 656, 774, 210/805, 806, 198.2, 259, 294, 511, 260/412, 412.8, 428.5

[56] References Cited

U.S. PATENT DOCUMENTS

| | | | |
|---|---|---|---|
| 4,260,639 | 4/1981 | Zosel | 426/478 |
| 4,675,132 | 6/1987 | Stout et al. | 260/412.8 |
| 4,692,280 | 9/1987 | Spinelli et al. | 260/420 |

FOREIGN PATENT DOCUMENTS

| | | | |
|---|---|---|---|
| 61-225139 | 10/1986 | Japan . | |
| 61220702 | 10/1986 | Japan . | |
| 62-72793 | 4/1987 | Japan | 260/412 |
| 62181398 | 8/1987 | Japan . | |
| 01108990 | 4/1989 | Japan . | |
| 01294649 | 11/1989 | Japan . | |
| 0225447 | 1/1990 | Japan . | |
| 641963 | 1/1979 | U.S.S.R. | 260/412 |

Primary Examiner—Stanley Silverman
Assistant Examiner—Krisanne Shideler
Attorney, Agent, or Firm—Browdy and Neimark

[57] ABSTRACT

Extraction and separation method and apparatus using a supercritical fluid for extracting a specified component from a sample by a supercritical fluid and introducing the supercritical fluid containing the extracted component into a silica gel column coated with silver nitrate so as to separate the extracted component.

By the combination of the extracting operation by a supercritical fluid under mild conditions and chromatography taking the advantage of the selectivity of the silica gel column coated with silver nitrate to olefins, the extract is obtained at a high concentration without producing denaturation.

4 Claims, 7 Drawing Sheets

EXTRACTION AND SEPARATION METHOD AND APPARATUS USING SUPERCRITICAL FLUID

BACKGROUND OF THE INVENTION

1. Field of the Invention

The present invention relates to extraction and separation methods and apparatus using a supercritical fluid, and, more particularly, to the improvement of the mechanism of separating the extracted component.

2. Description of the Related Art

A safe and inexpensive extraction method which is free from toxicity, harm and odor is demanded in the food, perfume, pharmaceutical and cosmetic industry fields, etc.

For example, fish oils contain about 10% of 5,8,11,14,17-eicosapentaenoic acid (hereinunder referred to as "EPA) having five double bonds or about 10% of 4,7,10,13,16,19-docosahexaenoic acid (hereinunder referred to as "DHA) having six double bonds as a fatty acid which constitutes triglyceride. An EPA methyl ester and a DHA methyl ester attract medical attention as a physiologically active substances which are effective as a remedy for arteriosclerosis and myocardial infarction.

Attempt has heretofore been made to concentrate and purify these methyl esters from methyl ester compounds of fish oils by fractional distillation, liquid chromatography or the like.

These methyl esters, however, have many double bonds in a molecule, so that they are susceptible to denaturation due to heat and oxygen.

Fractional distillation and liquid chromatography, which involve the step of heating and exposing the extract for a long time in the process of operation, produce a problem of denaturation.

As a technique of liquid chromatography, a method of separating and analyzing olefins, in particular, in the cis form by using a silica gel column coated with silver nitrate is known and a method of separating an EPA methyl ester or a DHA methyl ester by using this technique has been reported.

By this method, however, the substance being separated is apt to be denaturated by heat at the time of removing the organic solvent contained in the fraction.

As a countermeasure, extraction and separation by using a supercritical fluid of carbon dioxide, for example, which can be operated under comparatively mild conditions has recently gathered attention in place of fractional distillation and liquid chromatography.

A substance takes a solid, liquid or gas phase by varying the temperature and the pressure at a temperature below a predetermined critical temperature, but when the temperature exceeds the critical temperature, the substance cannot take a liquid phase any more however high pressure is applied thereto. A fluid in this state is called a supercritical fluid and has its characteristic physical properties which are not observed in general gas and liquid.

For example, the density of a supercritical fluid is several hundred times as high as that of a gas, rather closer to that of a liquid, but the viscosity thereof is substantially equal to that of a gas. The diffusion coefficient thereof is about 1/100 of that of a gas and several hundred time as large as that of a liquid.

Consequently, it is suggested that use of a supercritical fluid accelerates the movement, distribution and other physicochemical process of a substance more than use of a liquid. That is, use of a supercritical fluid as an extraction solvent or a mobile phase solvent can achieve more efficient extraction.

The conventional extraction and separation method and apparatus using a supercritical fluid, however, is disadvantageous in that a high concentration ratio cannot be obtained with respect to the components such as an EPA methyl ester and a DHA methyl ester.

SUMMARY OF THE INVENTION

Accordingly, it is an object of the present invention to eliminate the above-described problems in the related art and to provide extraction and separation method and apparatus using a supercritical fluid which are capable of separating an extract at a high concentration ratio while suppressing the degeneration of the extract.

As a result of studies undertaken by the present inventors so as to achieve this aim, it has been found that a high concentration ratio is obtained without producing a denaturation of the extract by combining the extracting operation under mild conditions which can be realized by use of a supercritical fluid and chromatography taking the advantage of the selectivity of a silica gel column coated with silver nitrate The present invention has been made on the basis of this finding.

In a first aspect of the present invention, there is provided an extraction and separation method and apparatus using a supercritical fluid comprising: an extraction process for extracting a specified component from a sample by the supercritical fluid; and a separation process for separating the extracted component by introducing the supercritical fluid containing the extracted component obtained by the extraction process into a silica gel column coated with silver nitrate.

In a second aspect of the present invention there is provided an extraction and separation method using a supercritical fluid comprising: an extraction process for extracting a specified component from an esterified fish oil by a supercritical fluid of carbon dioxide; and a separation process for separating an EPA methyl ester or a DHA methyl ester by introducing the supercritical fluid containing the extracted component into a silica gel column coated with silver nitrate so as to elute the EPA methyl ester by the supercritical fluid of carbon dioxide and the DHA ester by the supercritical fluid of carbon dioxide with alcohol added thereto.

In a third aspect of the present invention, there is provided an extraction and separation apparatus using a supercritical fluid comprising: an extraction portion for extracting a specified component from a sample by a supercritical fluid; and a separation portion including a silica gel column coated with silver nitrate and separating the specified component from the supercritical fluid containing the extracted component.

In a fourth aspect of the present invention, there is provided an extraction and separation apparatus using a supercritical fluid comprising: a fluid supply portion for supplying a supercritical fluid of carbon dioxide together with, as desired, an entrainer consisting of alcohol; an extraction portion for extracting a specified component from an esterified fish oil by the supercritical fluid of carbon dioxide supplied from the fluid supply portion; and a separation portion which includes a silica gel column coated with silver nitrate for introducing a supercritical fluid containing the extracted component thereinto and adsorbing and holding the extracted component and separating and eluting an EPA ester by the supercritical fluid and a DHA ester by the supercritical fluid and the entrainer, respectively.

According to the extraction and separation method and apparatus using a supercritical fluid of the present invention, since a specified component is extracted from a sample by a supercritical fluid, various components can be extracted at a high speed and with efficiency.

Since the supercritical fluid containing the extracted component is separated by a column coated with silver nitrate, olefins, in particular, olefins in the cis form can be separated mostly.

If the extracting operation is carried out by using a supercritical fluid of carbon dioxide in the method or apparatus of the present invention, it is possible to extract an EPA methyl ester and a DHA methyl ester contained in a methylesterified fish oil under mild conditions without the need for addition of specially high heat or long exposure in air, and to extract them without causing substantially any denaturation in spite of many double bonds.

By separating the extracted substance by using a silica gel coated with silver nitrate, it is possible to obtain an EPA methyl ester and a DHA methyl ester having a high purity by utilizing the peculiarity of the column coated with silver nitrate with respect to olefins in the cis form.

In this case, since the supercritical fluid of carbon dioxide is immediately evaporated at ordinary temperature and ordinary pressure, heating which is necessary in the prior art for the removal of an organic solvent in liquid chromatography or the like is also dispensed with.

Accordingly, neither of the methyl esters produces substantially any denaturation due to heat.

The above and other objects, features and advantages of the present invention will become clear from the following description of the preferred embodiment thereof, taken in conjunction with the accompanying drawings.

DESCRIPTION OF THE PREFERRED EMBODIMENT

A preferred embodiment of the present invention will be explained hereinunder with reference to the accompanying drawings, but it is to be understood that the present invention is not restricted to this embodiment.

Figure 1:
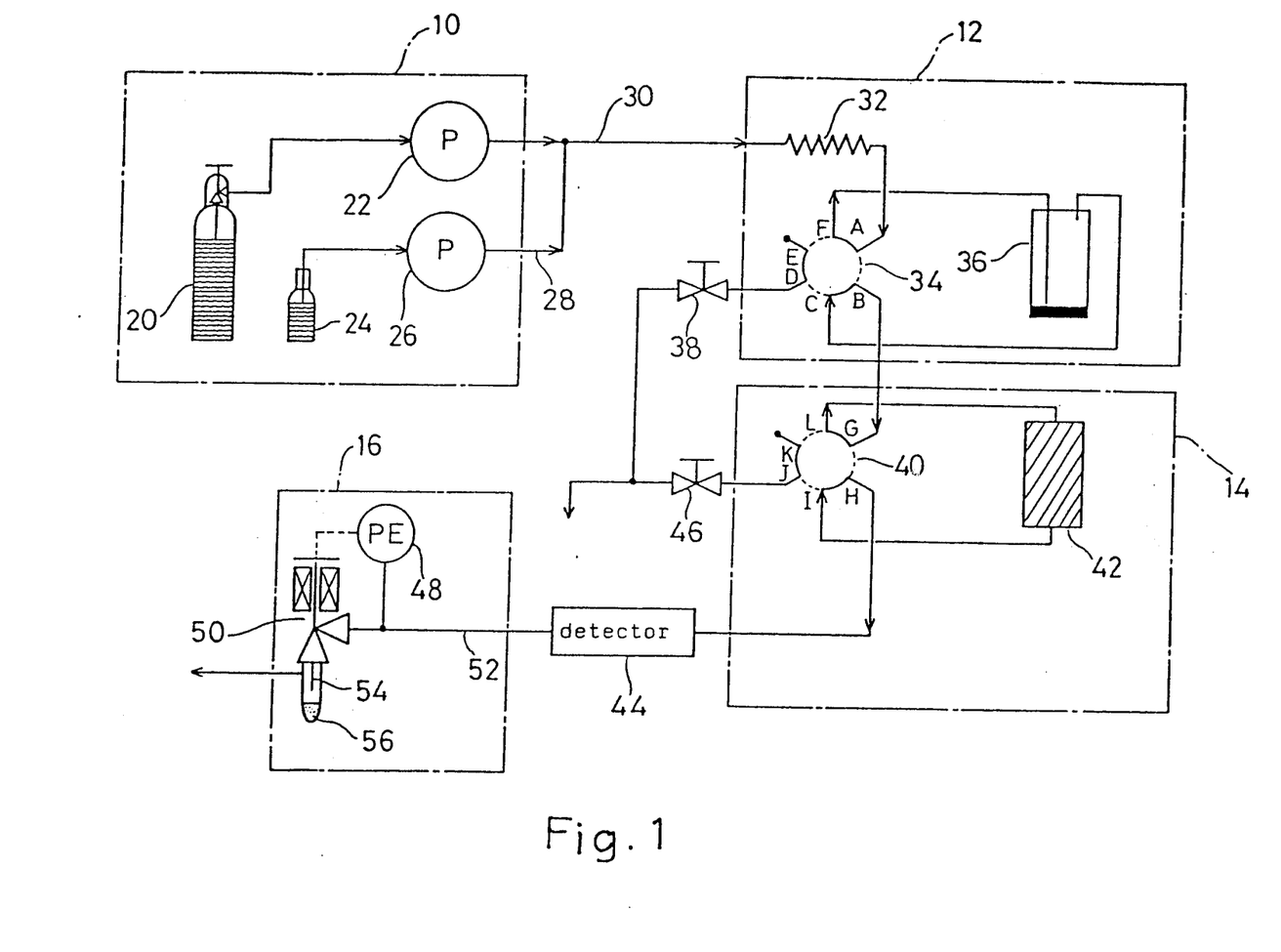
FIG. 1 is an explanatory view of an embodiment of an extraction and separation apparatus using a supercritical fluid according to the present invention.

FIG. 1 shows the structure of an embodiment of an extraction and separation apparatus using a supercritical fluid according to the present invention.

The extraction and separation apparatus shown in FIG. 1 includes a fluid supply portion 10, an extraction portion 12, a separation portion 14 and a fractionation portion 16.

The fluid supply portion 10 is composed of a carbon dioxide bomb 20, a pump 22 connected to the outlet of the bomb 20, an ethanol tank 24 and a pump 26 connected to the outlet of the ethanol tank 24.

A supply pipe 28 of the pump 26 is connected to a supply pipe 30 of the pump 22 so as to supply liquified carbon dioxide and ethanol, if necessary, to the extraction portion 12.

The extraction portion 12 is composed of a heat exchanger 32, a hexagon valve 34 and an extraction container 36.

The heat exchanger 32 heats the liquified carbon dioxide supplied from the supply pipe 30 to a temperature of 40° C. to change the carbon dioxide into the form of a supercritical fluid.

The hexagon valve 34 has ports A, B, C, D, E and F, and, in FIG. 1, the port A communicates with the port F, the port B with the port C and the port D with the port E, respectively.

The port A of the hexagon valve 34 is connected to the heat exchanger 32 and the port F is connected to the extraction container 36.

The supercritical fluid produced by the heat exchanger 32 is therefore supplied to the extraction container 36, wherein a predetermined extracting operation is carried out.

The discharge pipe of the extraction container 36 is connected to the port C. As described above, the port C is connected to the port B in FIG. 1, and the fluid flowing out of the extraction container 36 is supplied to the separation portion 14 through the hexagon valve 34.

The port D of the hexagon valve 34 communicates with air through a valve 38, and the port E is closed.

The separation portion 14 is composed of a hexagon valve 40 and a silica gel column 42 coated with silver nitrate.

The hexagon valve 40 has ports G, H, I, J, K and L, and, in FIG. 1, the port G communicates with the port L, the port H with the port I and the port J with the port K, respectively.

The supercritical fluid containing the extract and supplied from the extraction portion 12 is delivered to the column 42 coated with silver nitrate through the ports G and L, and the fluid flowing out of the column 42 coated with silver nitrate is supplied to the fractionation portion 16 through the ports I and H and a multiwavelength detector (MULTI-330) 44.

The port K of the hexagon valve 40 is closed and the port J communicates with air through a valve 46.

The fractionation portion 16 is composed of a pressure adjuster 48 and a pressure control valve 50.

The pressure adjuster 48 detects the back pressure of a pipe 52 through which the supercritical fluid of carbon dioxide containing the separated extract is delivered by way of a detector 44 and carries out feedback control so that the pressure in the pipe 52 is kept constant by controlling the opening degree of the pressure control valve 50.

The pressure control valve 50 has a small inner capacity so as to prevent trap due to the accumulation of the extracts.

An extract discharge pipe 54 connected to the pressure control valve 50 is connected to a fraction collector 56 for fractionation. The extraction and separation apparatus of this embodiment has substantially the above-described structure. The operation thereof will now be explained.

A desired sample is first charged into the extraction container 36. The pressure of the fractionation portion 16 is set at a pressure above the critical pressure, and the temperature of the heat exchanger 32 and the temperatures of the extraction container 36 and the column 42 coated with silver nitrate, if necessary, are maintained at a temperature above the critical temperature.

Liquified carbon dioxide is then supplied from the carbon dioxide bomb 20 of the fluid supply portion 10 to the extraction portion 12 by the pump 22. At this stage, the pump 26 has not been driven yet, so that ethanol is not supplied from the ethanol tank 24.

When the liquified carbon dioxide in the supply pipe 30 reaches the heat exchanger 32, the temperature of the carbon dioxide becomes higher than the critical temperature, thereby constituting a supercritical fluid. The supercritical fluid carbon dioxide is supplied to the extraction container 36 through the ports A and F of the hexagon valve 34, and extracts each component from the sample.

Since a supercritical fluid is quicker to move and disperse than a liquid, as described above, efficient extraction is carried out.

In addition, since the temperature for the extraction is about 40° C., denaturation due to heat is scarcely caused.

The supercritical fluid which has completed extraction is delivered again to the hexagon valve 34 and supplied to the hexagon valve 40 of the separation portion 14 through the ports C and B.

The hexagon valve 40 supplies the supercritical fluid containing the extracted components to the column 42 coated with silver nitrate through the ports G and L.

Due to the interaction between the silver ions and the olefins, especially, in the cis form, the olefins in the cis form are adsorbed and separated favorably in the column 42 coated with silver nitrate.

The hexagon valve 34 is then so operated that the communication of the passages A-B, C-D and E-F represented by the broken lines in FIG. 1 are established, respectively.

As a result, the extraction container 36 is separated from the passage of the supercritical fluid, and the supercritical fluid carbon dioxide is directly supplied from the heat exchanger 32 to the column 42 coated with silver nitrate 42 through the hexagon valves 34 and 40.

The components adsorbed by the silica gel coated with silver nitrate in the column 42 are successively separated and discharged in the order of the solubility in the supercritical fluid carbon dioxide, and are supplied to the fractionation portion 16 through the hexagon valve 40 and the detector 44.

By adjusting the pressure adjuster 48 of the fractionation portion 16 so as to raise the pressure sequentially and thereby vary the solubilities of the respective components adsorbed by the column 42, more reliable and efficient fractionation is enabled.

Furthermore, it is also possible to elute a DHA methyl ester, for example, in a good state by supplying a small amount of ethanol as an entrainer from the ethanol tank 24 through the pump 26, if necessary.

Active extraction and fractionation of an EPA methyl ester and a DHA methyl ester from a fish oil by using the apparatus of this embodiment will now be explained.

The column 42 coated with silver nitrate was prepared by dissolving 1 g of silver nitrate in 50 ml of acetonitrile, dispersing 10 g of silica gel (diameter: 10 to 20 µm, pore size: 60 Å) in the solution by ultrasonic, solidifying the solution under a reduced pressure, and charging 6 g of the thus-obtained product into a stainless steel pipe (inner diameter: 10 mm, length: 125 mm) in a dry state. A capillary gas chromatograph (5890A, produced by HP) was used for testing the purity of each fraction. The sample was dissolved in hexane or dichlorlomethane in the ratio of 10 mg/ml or 20 mg/ml, and 1 µl of the solution was used.

Figure 2:
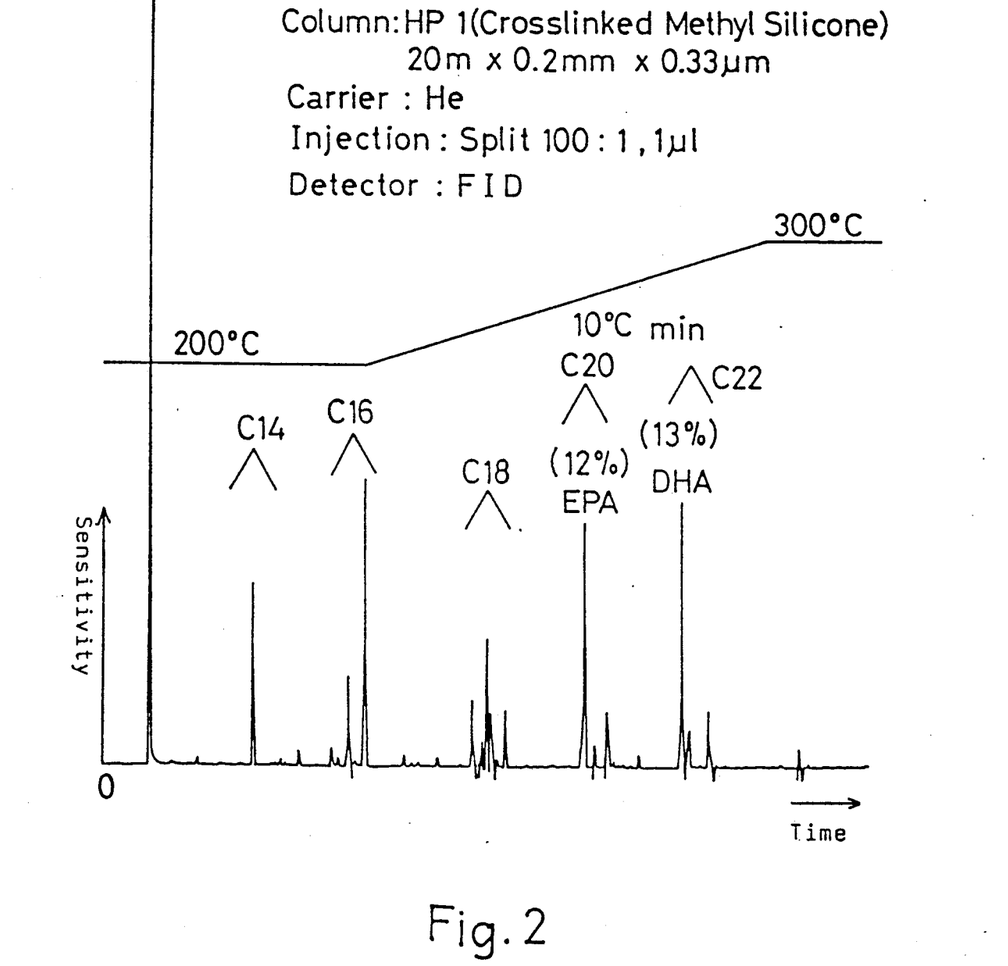
FIG. 2 is an explanatory view of the results of gas chromatography analysis of a methylesterified fish oil.

FIG. 2 shows the results of analysis of the methylesterified fish oil by the gas chromatograph.

As is clear from FIG. 2, each group of $C_{14}$ to $C_{22}$ was prominently observed, and the area ratio of an EPA methyl ester to all the peaks except the peak of the solvent was 12%, and the area ratio of a DHA methyl ester thereto was 13%.

Thereafter, 0.5 ml (0.445 g) of a methyl ester of a fish oil was charged into the extraction container 36 of the apparatus of the embodiment so as to carry out extraction and separation by using supercritical fluid carbon dioxide. The extraction container 36 was connected to the column 42 for 20 minutes under the conditions that the flow rate of liquified carbon dioxide was 9 ml/min. and the pressure of the column 42 at the exit was 80 atm. The components extracted during this time were adsorbed and held by the column 42.

The fluid passage was then separated from the extraction container 36 and this state was held for 160 minutes more.

A first fraction was collected during 110 minutes after the start of operation, and a second fraction was collected during the period from 110 minutes to 180 minutes after the start of operation.

The pressure of the column 42 at the exit was then raised to 120 atm. and a third fraction was collected for 70 minutes.

The pressure of the column 42 at the exit was next raised to 200 atm. and a fourth fraction was collected for 60 minutes.

Finally, a fifth fraction was collected for 60 minutes while maintaining the pressure of the column 42 at the exit at 200 atm. and under the conditions that the flow rate of the liquified carbon dioxide was 5 ml/min. and the flow rate of ethanol was 0.1 ml/min.

The results of gas chromatography analysis of the respective fractions obtained in the above-described way are shown in FIGS. 3 to 7.

Figure 3:
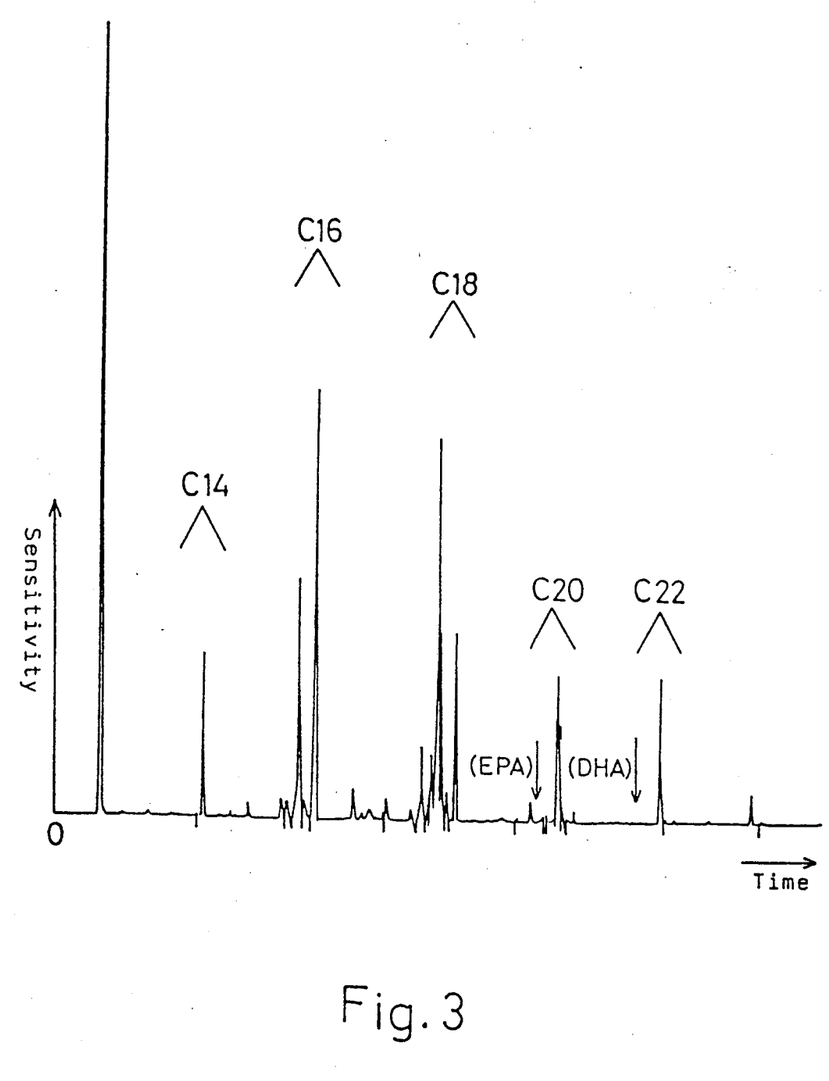
FIG. 3 is an explanatory view of the results of gas chromatography analysis of a first fraction collected by the embodiment of an apparatus according to the present invention.

FIG. 3 shows the result of analysis of the first fraction by gas chromatography. As is clear from FIG. 3, $C_{16}$ and $C_{18}$ are contained and small amounts of $C_{14}$, $C_{20}$ and $C_{22}$ are also eluted but any peak which corresponds to an EPA methyl ester or a DHA methyl ester is not observed.

Figure 4:
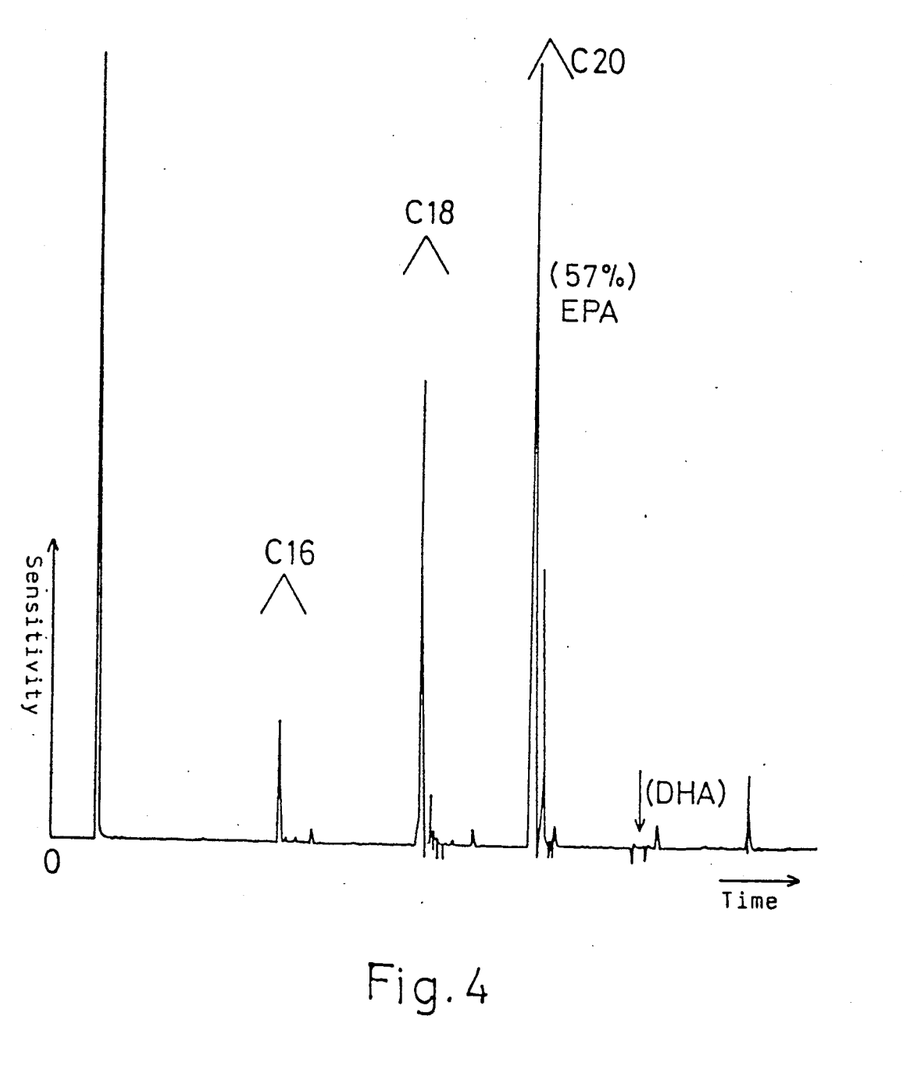
FIG. 4 is an explanatory view of the results of gas chromatography analysis of a second fraction collected by the embodiment of an apparatus according to the present invention.

In contrast, in FIG. 4 showing the result of analysis of the second fraction by gas chromatography, an EPA methyl ester occupies 57% as the main ingredient. However, $C_{16}$, $C_{18}$ and $C_{20}$ are also observed and the total amount thereof is 39%.

Figure 5:
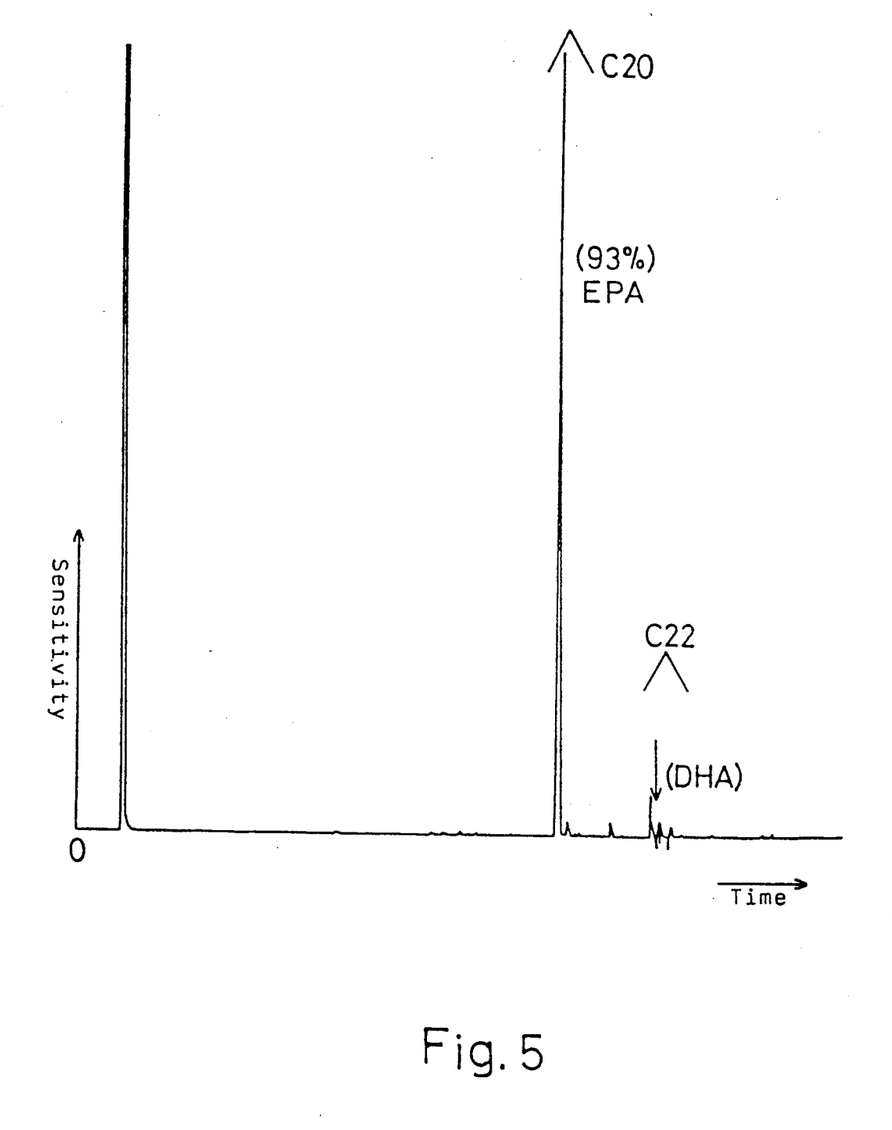
FIG. 5 is an explanatory view of the results of gas chromatography analysis of a third fraction collected by the embodiment of an apparatus according to the present invention.

FIG. 5 shows the result of analysis of the third fraction by gas chromatography. An EPA methyl ester occupies 93% as the main ingredient. Although a small amount of $C_{22}$ is eluted, any peak which corresponds to a DHA methyl ester is not observed.

Accordingly, it is possible to obtain an EPA methyl ester having a high purity by collecting the third fraction.

Figure 6:
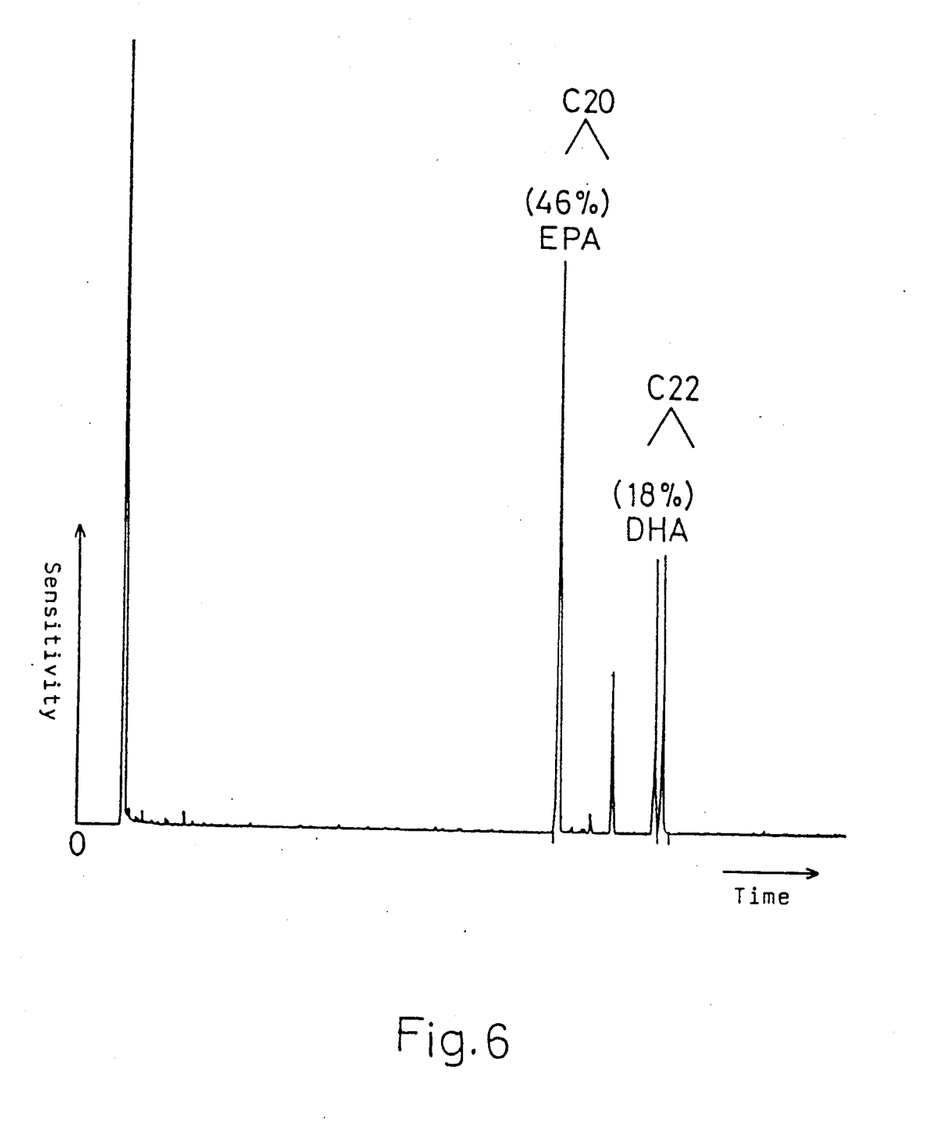
FIG. 6 is an explanatory view of the results of gas chromatography analysis of a fourth fraction collected by the embodiment of an apparatus according to the present invention.

FIG. 6 shows the result of analysis of the fourth fraction by gas chromatography. An EPA methyl ester occupies 46%, a DHA methyl ester 18% and the peak observed after the DHA methyl ester occupies 20%.

It cannot therefore be said that either of the EPA methyl ester and the DHA methyl ester has a high purity.

Figure 7:
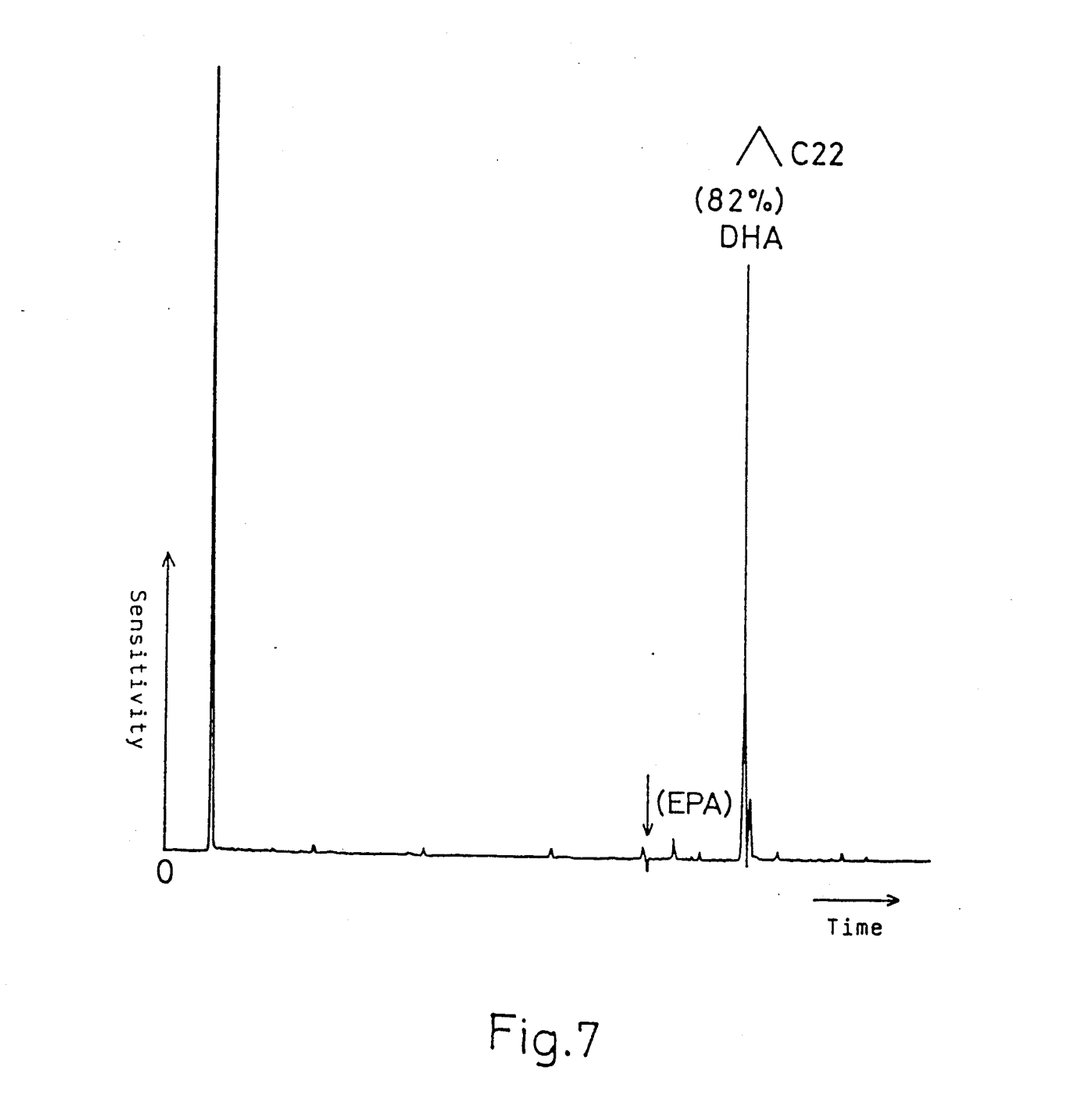
FIG. 7 is an explanatory view of the results of gas chromatography analysis of a fifth fraction collected by the embodiment of an apparatus according to the present invention.

However, a DHA methyl ester occupies 82% in the fifth fraction, as shown in FIG. 7. An EPA methyl ester scarcely exists and the peak observed after the DHA methyl ester in FIG. 4 is suppressed only to 7%.

It can therefore be understood from FIG. 7 that a DHA methyl ester can be obtained at a high purity from the fifth fraction.

These results are collectively shown in Table 1.

TABLE 1

| Object of analysis | Total amount (mg) | EPA methyl ester Wt % | EPA methyl ester Content (mg) | DHA methyl ester Wt % | DHA methyl ester Content (mg) |
|---|---|---|---|---|---|
| Fish oil | 445 | 12 | 53.4 | 13 | 57.9 |
| Comp. Fraction | 352 | 13 | 45.8 | 13 | 45.8 |
| 1 | 88.9 | 0 | 0.0 | 0 | 0.0 |
| 2 | 13.1 | 57 | 7.5 | 0 | 0.0 |
| 3 | 12.2 | 93 | 11.3 | 0 | 0.0 |
| 4 | 2.6 | 46 | 1.2 | 18 | 0.5 |
| 5 | 47.8 | 0 | 0.0 | 82 | 39.2 |

In this way, according to the embodiment of extraction and separation method and apparatus using a supercritical fluid of the present invention, it is possible to separate and extract an EPA methyl ester and a DHA methyl ester contained in a methylesterified fish oil efficiently and at a high purity.

Although an EPA methyl ester and a DHA methyl ester are extracted from the methyl ester of the aliphatic acid of a fish oil in this embodiment, the present invention is not restricted thereto and is applicable to the extraction and separation of various components at a high purity, especially, olefins in the cis form from various materials.

As described above, according to the extraction and separation method using a supercritical fluid of the present invention, since extracting operation is carried out by the supercritical fluid and the supercritical fluid containing the extracted components are separated by the column coated with silver nitrate, it is possible to separate a specified component from various samples with efficiency under mild conditions.

By using the extraction method for extracting a specified component from a methylesterified fish oil by a supercritical fluid of carbon dioxide and separating the extract from the supercritical fluid containing the extract by the column coated with silver nitrate, it is possible to concentrate an EPA methyl ester and a DHA methyl ester at a high concentration.

By using an extraction and separation apparatus provided with an extraction portion for extracting a specified component from a sample by a supercritical fluid and a separation portion having a silica gel column coated with silver nitrate, it is possible to extract and separate a specified component from various samples at a high concentration.

Combination of an extraction portion using a supercritical fluid of carbon dioxide and a silica gel column coated with silver nitrate enables efficient extraction and separation of an EPA methyl ester and a DHA methyl ester from a methylesterified fish oil under mild conditions.

While there has been described what is at present considered to be a preferred embodiment of the invention, it will be understood that various modifications may be made thereto, and it is intended that the appended claims cover all such modifications as fall within the true spirit and scope of the invention.

What is claimed is:

1. A method of extracting, purifying and separating 5, 8, 11, 14, 17-eicosapentaenoic acid ester and 4, 7, 10, 13, 16, 19-docosahexaenoic acid ester from methyl esterified fish oil comprising:

extracting methyl esterified fish oil with a supercritical fluid to obtain a supercritical fluid containing extracted components;

introducing said supercritical fluid containing extracted components into a silica gel absorption column coated with silver nitrate and maintaining a fluid pressure of about 80 atmospheres; separating 5, 8, 11, 14, 17-eicosapentaenoic acid ester from said column by supplying supercritical fluid into said column at a pressure of 120 atmospheres; and separating 4, 7, 10, 13, 16, 19-docosahexaenoic acid ester from said column by supplying supercritical fluid and alcohol into said column at a pressure of about 200 atmospheres.

2. An extraction and separation method according to claim 1, wherein said extraction includes the step of extracting said fish oil with a supercritical fluid of carbon dioxide; and said separation includes introducing said supercritical fluid of carbon dioxide containing said extracted component into said silica gel column coated with silver nitrate so as to elute 5, 8, 11, 14, 17-eicosapentaenoic acid ester by said supercritical fluid of carbon dioxide and elute 4, 7, 10, 13, 16, 19 docosahexaenoic acid ester by said supercritical fluid of carbon dioxide and alcohol.

3. An extracting, purifying and separation apparatus for use with a supercritical fluid comprising:

a fluid supply portion for supplying a supercritical fluid or a supercritical fluid and an entrainer of alcohol;

an extraction portion which includes an esterified fish oil;

a separation portion which includes a silica gel column coated with silver nitrate;

a valve portion which can connect a portion supplying a supercritical fluid to an extraction portion or separation portion, and means for connecting the extraction portion to a separation portion when the extraction portion is selected; and a pressure control portion which can control pressure of the separation portion.

4. An extraction, purifying and separation apparatus according to claim 3 comprising:

a fluid supply portion for supplying a supercritical fluid of carbon dioxide or carbon dioxide and an entrainer of alcohol;

an extraction portion for extracting a component from said esterified fish oil by said supercritical fluid of carbon dioxide supplied from a fluid supply; and a silica gel column coated with silver nitrate for introducing carbon dioxide supercritical fluid containing an extracted component and separating and eluting 5, 8, 11, 14, 17-eicosapentaenoic acid ester by carbon dioxide supercritical fluid and 4, 7, 10, 13, 16, 19-docosahexaenoic acid ester by carbon dioxide supercritical fluid and an alcohol entrainer.

* * * * *